United States Patent
Hoornaert et al.

(10) Patent No.: US 7,801,273 B2
(45) Date of Patent: Sep. 21, 2010

(54) INDICATION OF PATIENT SKIN DOSE IN RADIOLOGY

(75) Inventors: Bart P. A. J. Hoornaert, Eindhoven (NL); Nicolaas Hylke Bakker, Eindhoven (NL); Andrew Howard Martin, Eindhoven (NL)

(73) Assignee: Koninklijke Philips Electronics N.V., Eindhoven (NL)

(*) Notice: Subject to any disclaimer, the term of this patent is extended or adjusted under 35 U.S.C. 154(b) by 144 days.

(21) Appl. No.: 12/160,223

(22) PCT Filed: Jan. 4, 2007

(86) PCT No.: PCT/IB2007/050019
§ 371 (c)(1),
(2), (4) Date: Jul. 8, 2008

(87) PCT Pub. No.: WO2007/080522
PCT Pub. Date: Jul. 19, 2007

(65) Prior Publication Data
US 2009/0003527 A1   Jan. 1, 2009

(30) Foreign Application Priority Data
Jan. 12, 2006   (EP) .................. 06100285

(51) Int. Cl.
*H05G 1/42* (2006.01)
(52) U.S. Cl. ........................................ 378/97
(58) Field of Classification Search .......... 378/62, 378/64, 65, 97, 108
See application file for complete search history.

(56) References Cited

U.S. PATENT DOCUMENTS

| | | | |
|---|---|---|---|
| 6,301,329 B1 | 10/2001 | Surridge | |
| 6,501,818 B1* | 12/2002 | Ali et al. | 378/4 |
| 2005/0111621 A1 | 5/2005 | Riker | |
| 2006/0280287 A1* | 12/2006 | Esham et al. | 378/65 |

OTHER PUBLICATIONS

Den Boer et al, "Real-Time Quantification and Display of Skin Radiation During Coronary Angiography and Intervention", Circulation, vol. 104, No. 15, Oct. 9, 2001, pp. 1779-1784.
Miller et al, "Minimizing Radiation-Induced Skin Injury in Interventional Radiology Procedure", Radiology Radiol. SOC. North America, vol. 225, No. 2, Nov. 2002, pp. 329-336.

(Continued)

*Primary Examiner*—Irakli Kiknadze

(57) ABSTRACT

The field of the invention is diagnostic and interventional radiology and the invention is a dose indicator for use in a system for performing radiological procedures using ionizing radiation, for indicating a dose of radiation received in an area of skin by a subject during the radiological procedure, in which a zone is displayed which is representative of the extent of the area of skin exposed, and in which is a value of dose is displayed which is associated with the zone. The value of dose is representative of the dose of radiation received in the area of skin exposed during the procedure. The display is easily and quickly understood allowing the user of the system to swiftly understand the skin dose accrued by the patient. The use of zones provides an intuitive display.

19 Claims, 7 Drawing Sheets

OTHER PUBLICATIONS

Meyer et al, "Feasibility of a Semiconductor Dosimeter to Monitor Skin Dose in Interventional Radiology", Medical Physics, AIP, vol. 28, No. 10, Oct. 2001, pp. 2002-2006.

Bertrand (Coordinator), Coronary Arteriography, Nomenclature of the Arteries, Codifaction of Lesions, by the Working Group "Functional Evaluation and Angiography of the French Society of Cardiolgy", 1979.

Fletcher et al, "Comparison of Four Techniques to Estimate Radiation Dose to Skin During Angiographic and Interventional Radiology Procedures", SCVIR, 2002, pp. 391-397.

Morrell et al, "Calibration of Kodak EDR2 Film for Patient Skin Dose Assessment in Cardiac Catheterization Procedures", PHYS. MED. BIOL. 49, 2004, pp. 5559-5570.

Chugh et al, "A Computer-Graphic Display for Real-Time Operator Feeddback During Interventional X-Ray Procedures", Visualization, Image-Guided Procedures and Display, vol. 5367, No. 1, Feb. 2004, pp. 464-473.

Balter et al, "Techniques to Estimate Radiation Dose to Skin During Fluoroscopically Guided Procedures", Skin Dose Measurements AAPM, Jul. 2002, pp. 1-10.

* cited by examiner

New 2 : zone dose rate t=0 t=0+Δt t=0+2Δt t=0+3Δt t=0+4Δt

INDICATION OF PATIENT SKIN DOSE IN RADIOLOGY

The invention relates to a dose indicator for use in a system for performing radiological procedures using ionizing radiation, for indicating a dose of radiation received in an area of skin by a subject during the radiological procedure.

Ionizing radiation is used in medicine for the acquisition of images of the body both for the purposes of diagnosis and, under special circumstances, for the guiding of interventional equipment during radiological and surgical interventions. Radiological images are performed currently on both radiographic equipment, by which the image is stored, and fluoroscopic equipment, in which the image is not stored.

Interventional radiology (IVR) uses imaging technology to form clinically relevant images of a patient while an interventional procedure, usually surgical, is underway. Prior to this the same equipment is often used to form a series of diagnostic images of the patient for the purposes of ascertaining if full intervention is warranted. Such diagnostic images as are acquired under these circumstances usually involve the use of radiographic dye and guide wires. The images acquired during both the diagnostic acquisition and the interventional acquisition allow accurate localization of any guidewires or interventional equipment and any surgical instruments used in the procedure. The overwhelming majority of IVR procedures are undertaken using ionizing radiation which provides real time images, displayed quickly for the user, and which contain sufficient contrast to allow visual differentiation of surgical equipment from human tissue. An example is the use of fluoroscopy while performing balloon catheterization of an arterial stenosis or a stent placement.

The image contrast and detail required in the resulting images, both for diagnosis and subsequent intervention, often necessitates the use of an X-ray beam at sufficient beam parameters to cause high doses in the patient. This occurs in part because of the length of time taken to complete the interventional procedure in combination with the $kV_p$ of the beam. Other factors also influence the overall doses received by the patient, as is known in the art. Much effort has been invested by manufacturers of equipment used in IVR into providing users with accurate information about radiation doses absorbed by the patient undergoing the procedure. In particular, if the surgeon or radiologist performing the procedure can be informed of the patient doses accrued during the intervention they can make more informed decisions about how to successfully complete the procedure while keeping patient dose to a minimum.

The absorption in matter, including living tissue, of both X-rays and gamma radiation is essentially stochastic in nature and with this is concomitant stochastic damage to any living tissue exposed to ionizing radiation. The stochastic effects of radiation are those whose occurrence is a statistical function of the absorption of radiation and include the induction of cancer through radiation exposure, a process known as radiocarcinogenesis. As is known in the art, terms associated with stochastic effects are absorbed dose, equivalent dose and effective dose.

However, sufficiently high dose rates of radiation can be absorbed by tissue at a rate high enough to cause non-stochastic tissue damage. This non-stochastic damage, known as deterministic effects, occur above certain thresholds and once the threshold is exceeded the severity of the effect increases with increasing dose. Radiation sickness is a deterministic effect. Of importance radiologically are the deterministic effects of radiation to the surface of the human body during radiological procedures. Deterministic effects on the skin include early transient erythema, occurring at 2 Gy, temporary epilation, occurring at 3 Gy, permanent epilation, occurring at 7 Gy and dry desquamation, occurring at 14 Gy. The values quoted are known to be approximate. As is known in the art, terms associated with deterministic effects are entrance skin dose and Air Kerma.

A survey of literature, e.g. Minimizing radiation-induced skin injury in interventional radiology procedures, Radiology 2002; 225; 329-336, and Calibration of Kodak EDR2 film for patient skin dose assessment in cardiac catheterization procedures, Morrell et al., Phys. Med. Biol. 2004; 49; 5559-5570, reveals that reduction of patient dose during interventional radiology procedures is important for overall patient health and that an important step in the reduction of patient dose is the provision and display to the user of relevant information concerning the dose to the patient. In particular, skin injury, as a deterministic effect of radiation, can be reduced if information regarding the skin dose is available to the surgeon.

The Siemens Caregraph system is a product designed to indicate skin dose to the patient during an IVR procedure and is described in several publications, e.g. Techniques to estimate radiation dose to skin during fluoroscopically guided procedures, Balter et al., Skin Dose Measurements AAPM July 2002; Comparison of Four Techniques to Estimate Radiation Dose to Skin During Angiographic and Interventional Radiology Procedures, Fletcher et al. SCVIR, 2002, pages 391 to 397. It consists of a screen display showing an area of patient skin surface folded out into a flat two dimensional image on which is displayed the dose absorbed by each 0.5 cm$^2$ patch of skin exposed. Each patch is color coded to indicate the dose absorbed to the nearest interval and a key is shown indicating the range of dose intervals plotted and the color with which each is depicted. The Siemens Caregraph is currently considered the most accurate product which indicates dose to the patient. However, as an indicator of dose it is difficult to understand quickly and far too difficult to understand by a user in the process of performing an interventional procedure.

It is an object of the invention to provide an indicator of dose to the patient which provides dose information to the user which can be quickly understood by the viewer.

This is achieved according to the invention whereby the dose indicator is arranged to display a zone representative of the extent of the area of skin exposed, and further arranged to display a value of dose associated with the zone, which value of dose is representative of the dose of radiation received in the area of skin exposed during the procedure.

The value of dose displayed may be measured or may be calculated, as is known in the art, and provides the user with a simple and easily understood indication of the dose received in the area of skin represented by the zone.

The dose indicator therefore shows the user a significantly reduced amount of information and further, displays the information in such a way that it is associated with a representative image of patient skin which is instantly clinically recognizable.

The information is therefore easily absorbed on a cognitive level by the user. The user of the system, the surgeon or radiologist, has very little time, in fact typically only split seconds, in which to absorb any offered information concerning the absorbed dose to the patient while trying simultaneously to absorb the visual information depicted in the image of the procedure. By showing in effect only a single value of dose the user is provided with salient information without being overloaded with information. By associating the dose shown with a zone representative of the area being exposed, the user can instantly see and comprehend the relevance of the dose information displayed.

Further the zone can be depicted as the commonly sized area of skin on the patient exposed during the IVR procedure in the commonly used rotation and angulation applied within the system for the procedure. This feature allows the user to see the information presented in a way which is instantly clinically relevant and recognizable and further enhances the comprehensibility of the information displayed.

The value of dose can be displayed graphically.

A particularly useful measure of dose which can be displayed using the invention is the Air Kerma value of dose.

The size of the zone, being representative of the area of skin exposed by radiation, represents a area of skin which is typically exposed in the procedure undertaken. It is found that using a zone which represents an area of skin which is at least 10 cm by 10 cm is particularly useful and covers a size of skin commonly exposed by interventional procedures.

The dose indicator can be arranged to indicate when the value of dose passes a threshold. Commonly this will be a threshold for deterministic skin effects and will serve as a warning to the surgeon that any further exposure to the same area of skin, even if clinically necessary for the completion of the procedure, is likely to induce deterministic skin effects in that particular area of skin.

The invention also relates to a system for the performance of radiological procedures using ionizing radiation on a subject, the system comprising imaging apparatus for the performance of a radiological procedure on a subject in which an area of skin of the subject is exposed to a dose of radiation, and also comprising display apparatus arranged to display a zone representative of the extent of the area of skin exposed, and further arranged to display a value of dose associated with the zone, which value of dose is representative of the dose of radiation received in the area of skin exposed during the procedure. Such a system has the advantage that it incorporates a dose indicator according to the invention and is therefore suitable for use in interventional radiology while providing the user with information which is quickly understood concerning the dose to the patient.

The invention also relates to a user interface for a system for performing radiological procedures comprising a dose indicator according to the invention. Such a user interface allows the dose indicator to be applied to any user interface used for driving and operating radiological apparatus that uses ionising radiation. Further, the invention also relates to a workstation for a system for performing radiological procedures comprising a dose indicator according to the invention. Such a workstation allows the dose indicator to be applied to any user interface used for driving and operating radiological apparatus that uses ionising radiation.

The system may be arranged to display the dose indicator on the same screen used to display the images from the interventional procedure. This has the advantage that the surgeon using the images to guide his or her procedure can see and quickly understand the dose to the patient in the area of skin under exposure without taking his or her eyes off the screen.

The invention, while explained chiefly in terms of its application to radiographic and fluoroscopic equipment suitable for interventional procedures, can in fact be applied to any radiographic equipment which uses ionizing radiation. It could indeed be applied to an X-ray unit used for taking standard chest X-rays, for instance. The power of the invention lies in its ability to communicate information about patient skin dose in a manner which is quickly and easily understood and which is intuitive and can therefore be applied to any radiological equipment used for patient exposure under circumstances when the user or clinician wishes to quickly and easily understand the accrued patient skin dose.

The invention is further explained using the following figures.

Figure 1:
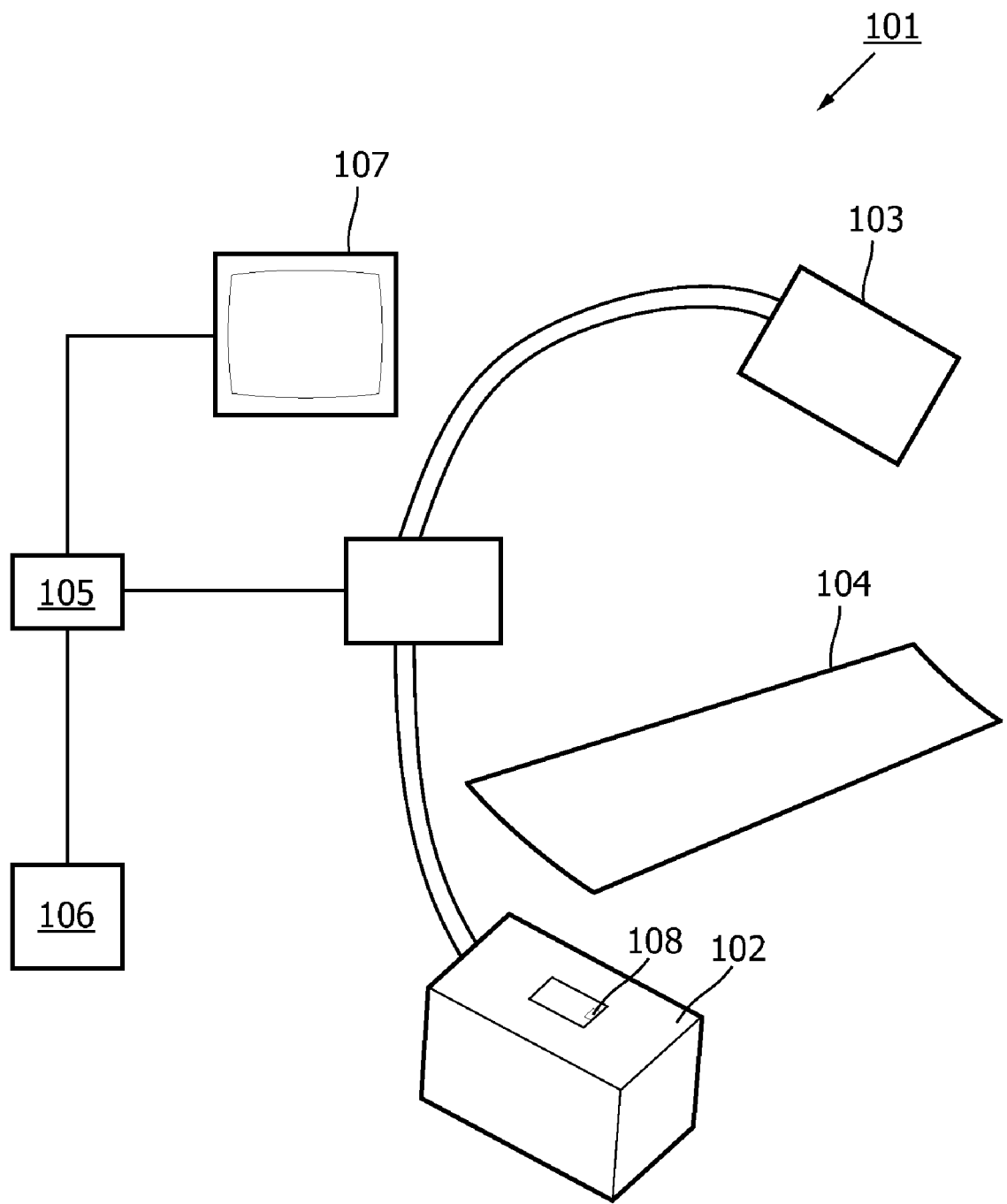
FIG. 1 shows a typical X-ray unit suitable for the performance of interventional radiology and therefore suitable for the application of the invention.

FIG. 1 shows a typical X-ray unit 101 suitable for the performance of interventional radiology. The unit consists of an X-ray source 102 and X-ray detector 103, a patient bed 104 for placement of the patient, a control unit 105 for controlling the rotation and angulation of the X-ray source, and correspondingly the X-ray detector, an input point 106 by which the user or users can input instructions to control the rotation and angulation of the source and control the operation of the source, and display apparatus 107 by which the user can view the image acquired by the X-ray unit.

In typical performance, the patient is placed on the bed 104 and the user acquires images of the patient while performing an interventional procedure. The display of the images on the display apparatus 107 during the interventional procedure allows the user to perceive the progress of the interventional procedure. The user controls the operation of the X-ray source, in other words, switches it on and off, controls the $KV_p$ of the source and the size of the collimator jaws, using the input point 106. The input point 106 can also be used to control the position of the X-ray source, which is for example the rotation of the X-ray source around the central axis of the patient and the angulation of the X-ray source around an axis perpendicular to a sagittal plane of the patient. As is known in the art, individual manufacturers of equipment vary in their exact definitions of rotation and angulation.

The input point may be any device suitable for the input of information to the control unit 105 and therefore may be for example a handset, a keyboard or a foot operated device. A voice operated input point is also possible, as is known in the art.

The X-ray unit 101 typically includes a dose measurement device 108 for the measurement of radiation exposure from the source. The calculation of patient skin dose is known in the art and, for example, may typically be undertaken by the measurement of radiation exposure at a known point in the X-ray beam while the beam is switched on, using further extrapolation incorporating a single or series of known or assumed source to skin distances to arrive at a final measure of skin dose. Various methods to achieve this are known. The application of the invention requires that some measurement or calculation of dose is made which is representative of the dose received by the patient in the area of skin exposed during exposure.

Figure 2:
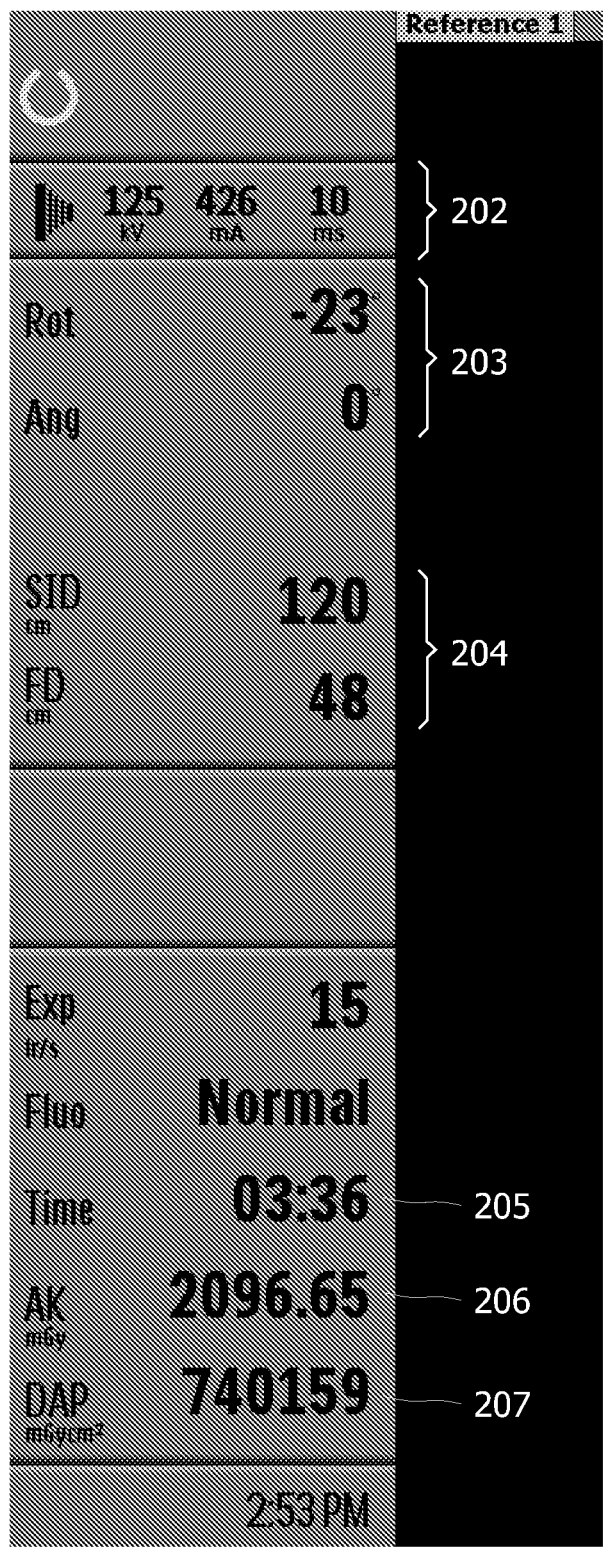
FIG. 2 shows a state of the art graphical display incorporating a dose indicator.

FIG. 2 shows a state of the art graphical display incorporating a dose indicator as has been commonly used. The display 201 includes details of the energy of the radiation beam 202, the geometrical orientation of the source relative to the patient 203, the distance between the source and the patient 204, the exposure time elapsed 205, the Air Kerma 206 and the Dose Area Product 207.

Figure 3:
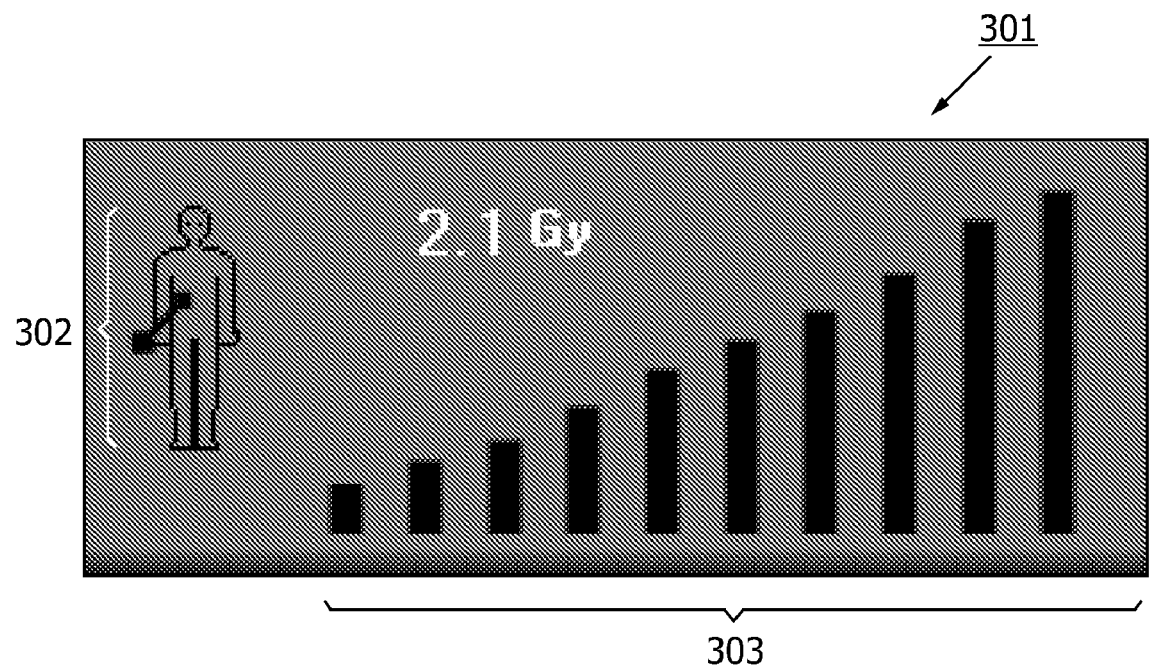
FIG. 3 shows an embodiment of a preferred graphical display.

FIG. 3 shows a dose indicator 301 comprising an indication of a zone 302 and a graphical display of the value of dose 303. This dose indicator can be clearly understood by the user and indicates the accrued dose in Air Kerma, shown by the bars of the graphical display 303, and also the skin area on the patient over which this dose has been absorbed, 302.

Figure 4:
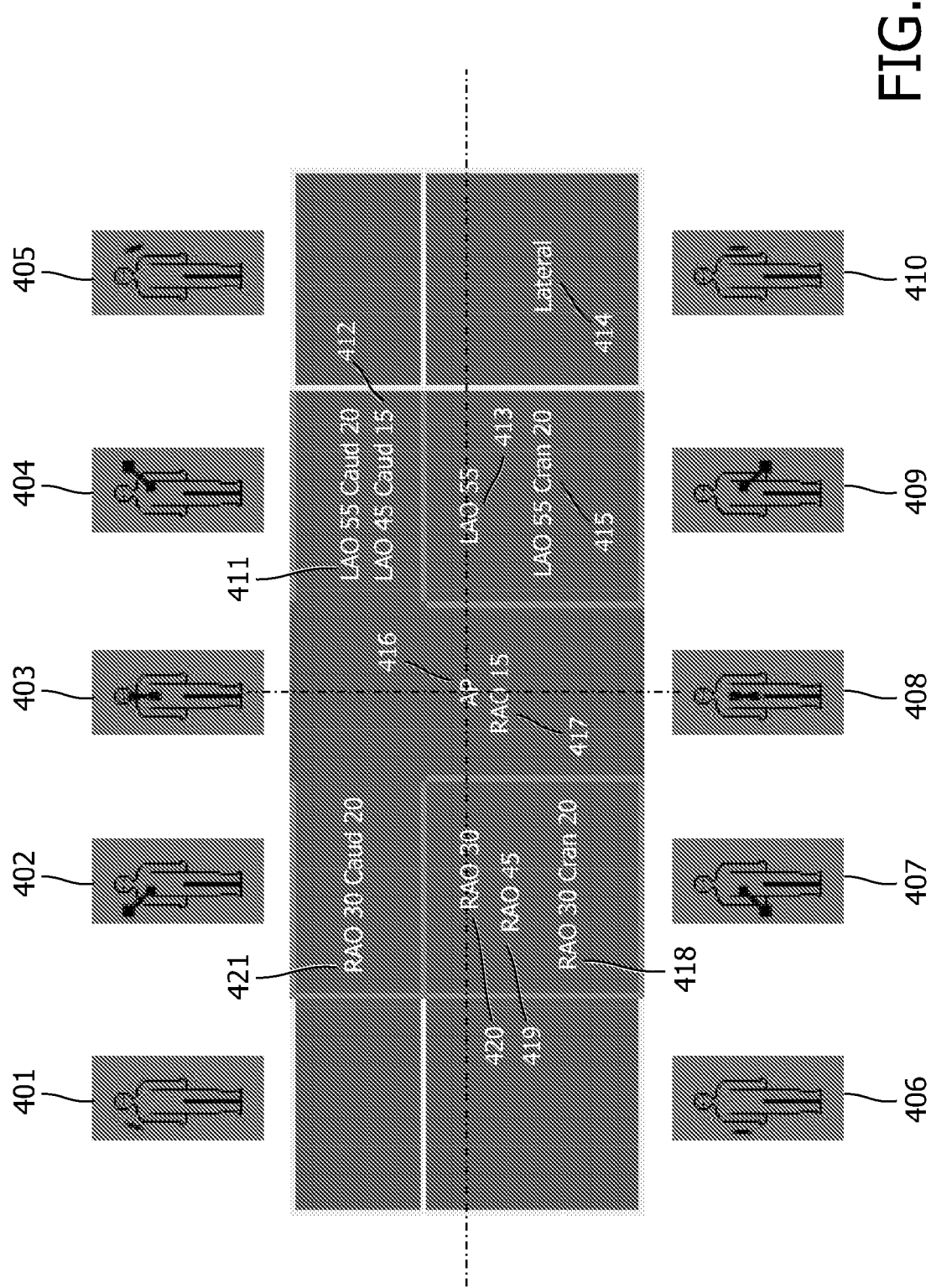
FIG. 4 shows an array of possible zones according to the invention.
Figure 5A:
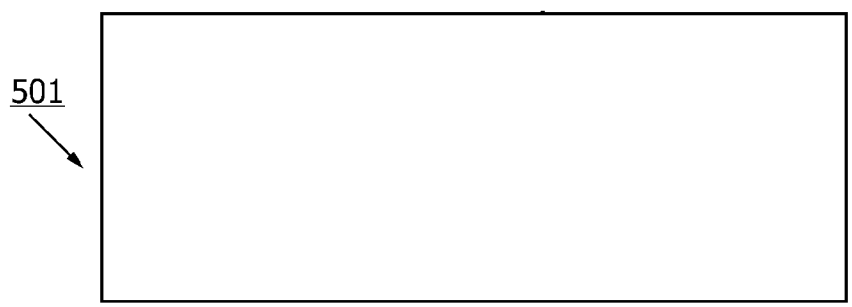
FIG. 5 shows an embodiment of a graphical display for the value of dose which has been found to be particularly effective.
Figure 5B:
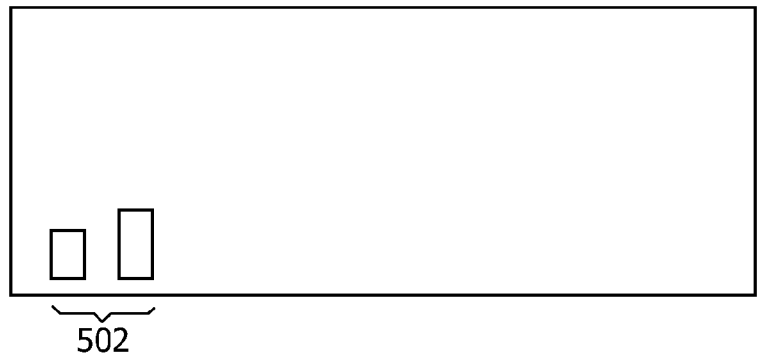
Figure 5C:
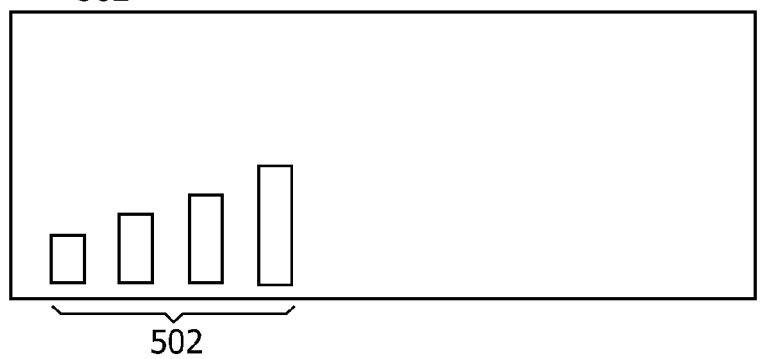
Figure 5D:
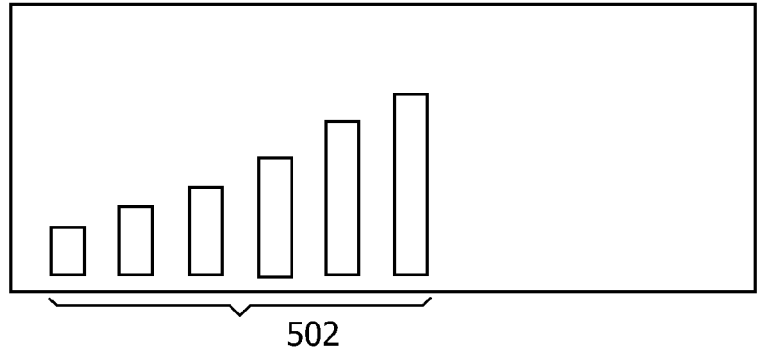
Figure 5E:
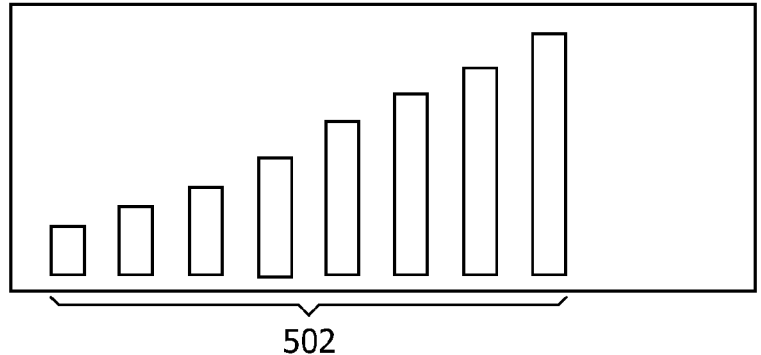

FIG. 4 shows an array of possible zones, 401 to 410, according to the invention. In this case these are zones representing the areas of skin on a patient commonly exposed in a cardiac procedure. In the case of cardiological procedures the cardiologist or radiologist typically wishes to view the three main coronary arteries, the circumflex, the right coronary artery and the left coronary artery. The three coronary arteries can usually be viewed in a series of standard image projections, as is known in the art, e.g. in 'Coronary Arteriography, Nomenclature of the Arteries, Codification of Lesions', by the Working Group "Functional Evaluation and Angiography of the French Society of Cardiology", Coordinated by M. E. Bertrand, 1979. The zones represent the commonly used projections, 411 to 421, and are the right anterior oblique projection at 30° (RAO 30°), item 420; the anterior-posterior projection (AP), item 416; the left anterior oblique projection at 55/60° (LAO 55/60°), shown here as LAO 55, item 413; left anterior oblique projection at 55/60° combined with cranial angulation of 20°, shown here as LAO 55 Caud 20, item 411; left lateral projection, item 414; left anterior oblique projection at 45° combined with a caudal angulation of 15°, item 412; right anterior oblique projection at 45° (PAO 45°), item 419. Also possible is right anterior oblique projection at 120° combined with a cranial angulation of 10°, unshown.

Each hospital or medical facility commonly uses a specific set of preferred orientations, often based on the clinical expertise of the individual users and also the specifics of the particular patient morphology with which they are presented. As is known in the art, these are standard projections with standard degrees of angulation and rotation used with radiographic and fluoroscopic equipment, but which often require small angular alterations on a patient by patient basis. The zones shown are indicators of the particular clinical orientations which may be used. In this way FIG. 4 shows 10 zones which can be displayed and which in each case can be used to depict the orientation used by the hospital in question.

Also possible are orientations at right anterior oblique 30° with an angulation of 20°, item 421; right anterior oblique at 30° with an angulation of 20°, item 418; right anterior oblique at 15°, item 417; and left anterior oblique at 55° with an angulation of 20°, item 415.

A different set of zones are used for applications of the invention to other diagnostic and interventional procedures. For example, when applied to cranial applications, the possible zones shown depict the commonly used orientations of the X-ray equipment which acquire images of the correct anatomy.

The use of zones, according to the invention, has the further advantage that the same standardized zones are displayed regardless of any small deviations from the standard projections that may be made during actual exposure of the patient. This simplifies the display greatly, from the point of view of the user of the system, and allows an understanding of the skin dose to the patient regardless of the actual angulation and rotation combination applied for any specific patient.

FIG. 5 shows an embodiment of a graphical display 501 for the value of dose which has been found to be particularly effective in indicating the value of dose clearly, quickly and effectively to the user of the interventional radiology system. The display 501 comprises a series of bars 502, graduated to show increasingly accrued skin dose up to a pre-determined threshold. The pre-determined threshold will normally be 2 Gy but may be decreased in the case of a patient who has a pre-accrued existing dose to the area of skin under exposure, and may also theoretically be increased in the case of a patient known to be radioresistant. As the particular exposure commences the bars 502 appear on the display 501 as the skin dose to the area under exposure increases to the levels represented by each bar 502. The user sees a series of bars 502, appearing one after the other, until all of the bars 502 are visible along the horizontal axis of the display. When the last bar 503 is visible the area of skin under exposure has received the threshold dose. FIG. 5 shows the display at t=0, at commencement of the exposure, and then at t=0+Δt, t=0+2 Δt, t=0+3 Δt and t=0+4 Δt. Where the time interval Δt between views of the display depends on the exposure rate of the beam of radiation.

Figure 6:
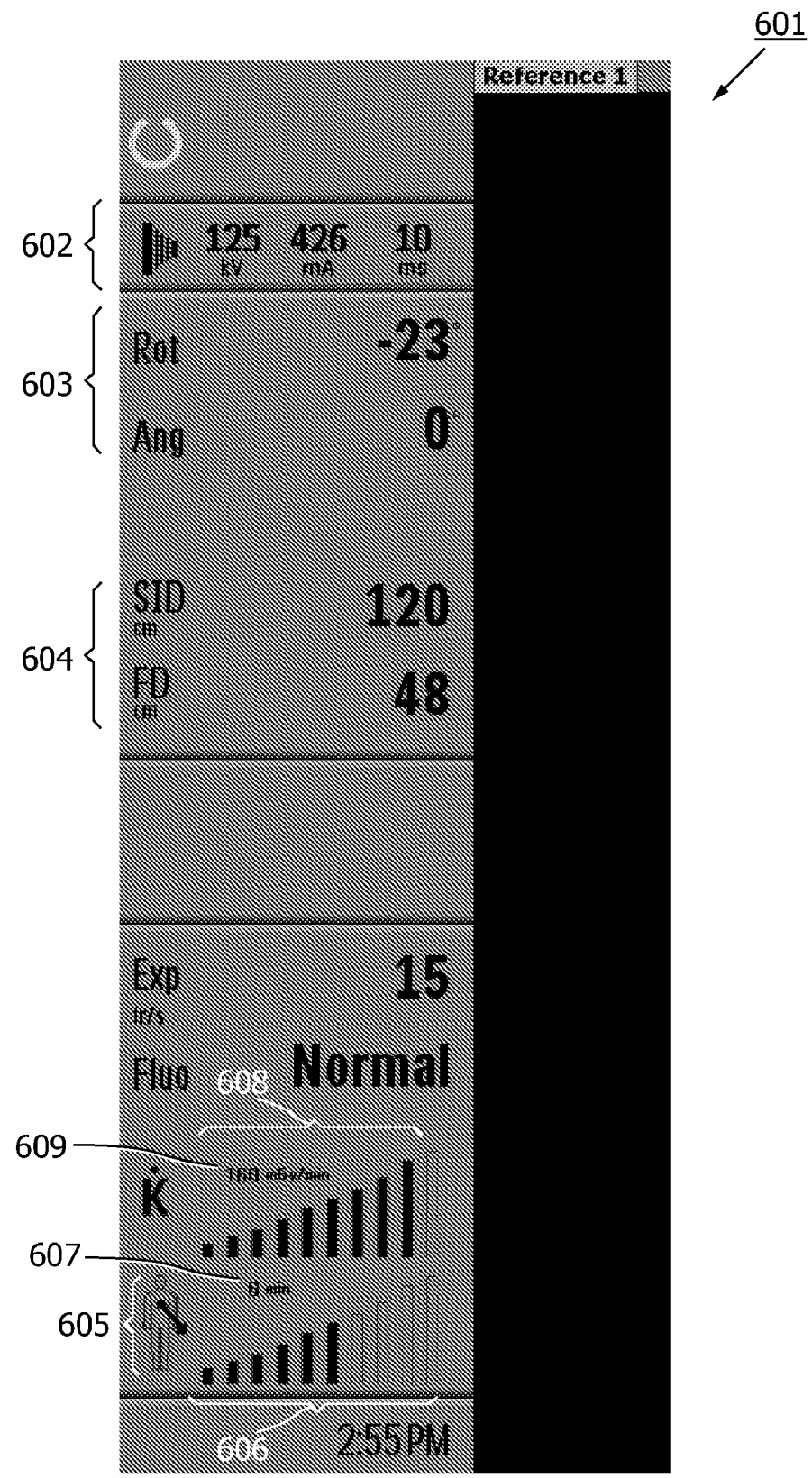
FIG. 6 shows how the invention, and in particular the embodiment of FIG. 5, might be incorporated into a visual display.

FIG. 6 shows how the invention, and in particular the embodiment of FIG. 5, might be incorporated into a visual display. FIG. 6 shows a display 601 comprising details of the energy of the radiation beam 602, the geometrical orientation of the source relative to the patient 603, the distance between the source and the patient 604, and in this case the zone representative of the extent of the area of skin exposed 605 and a value of dose associated with that zone 606. An extra, particularly advantageous embodiment is also shown. The skin dose rate is shown on the display as a numerical value 609, but also using substantially the same form of graphical display 608 as the value of dose 606. Taking together the skin dose rate and the skin dose accrued allows a predication to be made of the time remaining before the threshold is reached and this time can also be displayed 607, providing further useful information for the user. It is also possible to predict the dose rate for specific operational set-ups and the predicated time to threshold may be shown for these set-ups may be displayed, allowing the user to choose the optimal set-up for the specific requirements of the remaining parts of the procedure.

Figure 7:
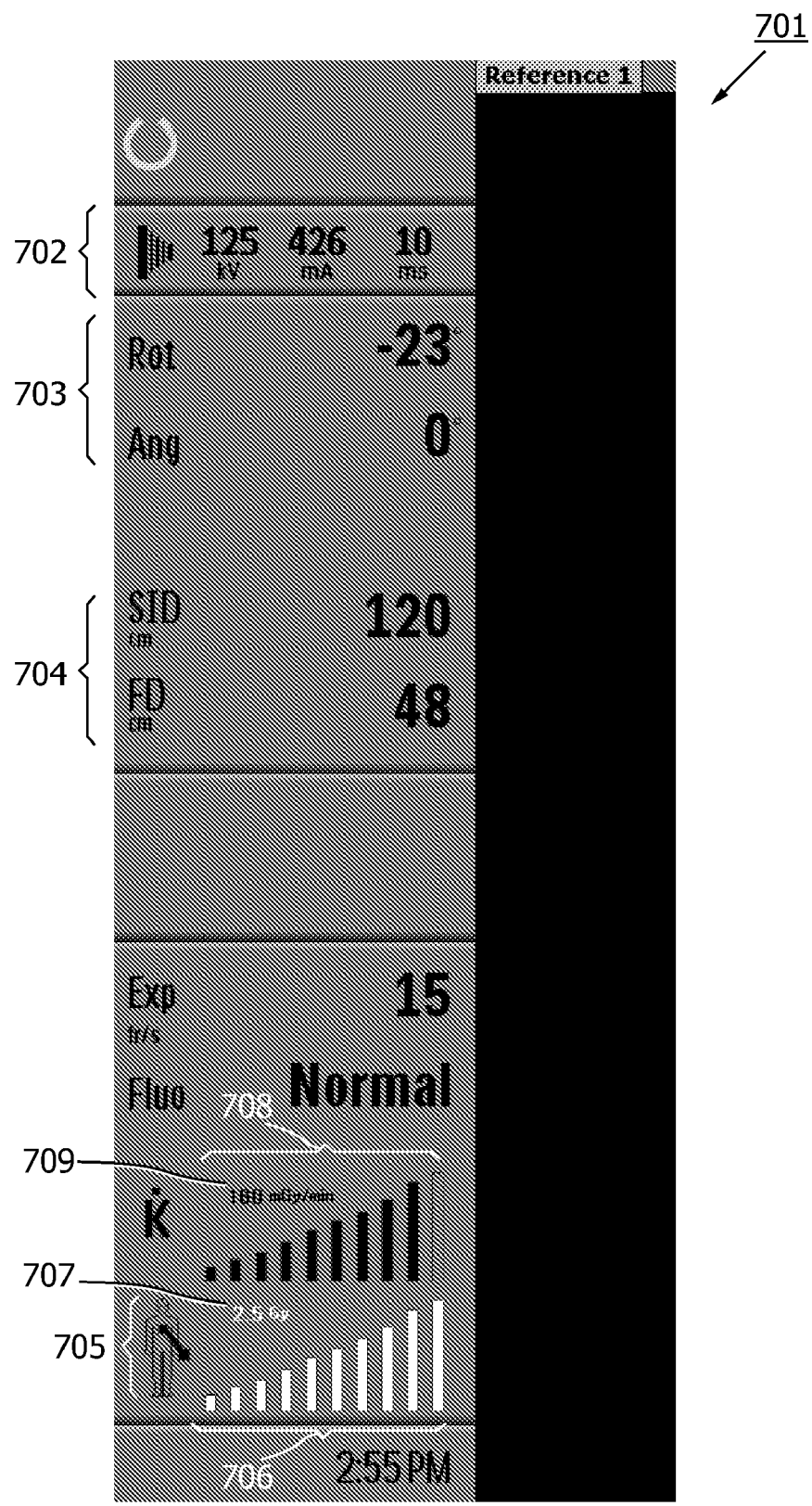
FIG. 7 shows how the invention, and in particular the embodiment of FIG. 5, might be incorporated into a visual display, incorporating the change in display after the passing of a predefined threshold.

FIG. 7 shows how the invention, and in particular the embodiment of FIG. 5, might be incorporated into a visual display, incorporating the change in display after the passing of a predefined threshold. FIG. 7 shows a display 701 comprising details of the energy of the radiation beam 702, the geometrical orientation of the source relative to the patient 703, the distance between the source and the patient 704, the zone representative of the extent of the area of skin exposed 705, and a value of dose 707, shown in a visually alerting color, indicating that a pre-defined threshold has been exceeded. This would occur when the bars shown in 606 of FIG. 6 have reached their maximum value. At this point the bars are shown in an equally visually alerting color 706 and remain at their maximum value, so showing the user that the threshold for that area of skin has been reached.

Alternatively, the form of the display may change, so that the bars do not remain on the display but are replaced by a warning symbol, for example. In another embodiment the bars are redisplayed from a value of zero but displayed now upside down. This has the advantage of being visually alerting, by being different from the previous display, while continuing to count up dose to a new, second, threshold. This has the advantage that the user can continue to receive information about the steadily accruing patient skin dose. The new bars can still be displayed in a visually alerting colour. The rate at which skin dose is accruing, 709, may also be shown.

Ultimately, the invention allows the clinical user of interventional radiological equipment to monitor easily, intuitively and understandably the dose to the patient and therefore reduces the risk of overexposure and concomitant injury to the patient.

The invention claimed is:

1. A system for performing radiological procedures using ionizing radiation on a subject, comprising:
    an imaging apparatus for performing a radiological procedure on a subject in which areas of skin of the subject are exposed to a dose of radiation; and
    a display apparatus that displays a graphical representation of an array of individually selectable zones representing the areas of skin exposed, wherein each zone is indicative of a different predetermined physical orientation of a subject for the radiological procedure, and the display apparatus alternatively displays a value of dose associated with only one of the zones when the one of the zones is selected, and the displayed value represents the dose received in an area of skin corresponding to the selected zone exposed during the procedure.

2. The system as claimed in claim 1 wherein the zones are depicted as the commonly sized areas of skin on the subject exposed during the procedure by use of commonly applied rotation and angulation of the imaging apparatus for that procedure.

3. The system as claimed in claim 1 further configured to display at least one image resulting from the procedure, wherein the zones and the values of dose are displayed on the same visual display screen of the display apparatus as the at least one image.

4. The system as claimed in claim 1 wherein the zones represent areas of skin which is at least 10 cm$^2$.

5. The system as claimed in claim 1 wherein the zones represent areas of skin which is at least 10 cm by 15 cm.

6. The system as claimed in claim 1, wherein the graphical representation is not a reconstructed image.

7. A computer-readable medium containing computer executable instructions, that when executed on a processor of computer, cause the computer to do the following acts:
    display a graphical representation of an array of individually selectable zones representing areas of skin of a subject exposed during a radiological procedure, wherein each zone is indicative of a different predetermined physical orientation of the subject for the radiological procedure, and alternatively display a value of dose associated with only one of the zones when the one of the zones is selected, and the displayed value represents the dose received in an area of skin corresponding to the selected zone exposed during the procedure.

8. The computer-readable medium as claimed in claim 7 wherein the zones are depicted as commonly sized areas of skin on the subject exposed during the IVR procedure by use of commonly used rotation and angulation applied within the system for the procedure.

9. The computer-readable medium as claimed in claim 7, wherein the graphical representation is not a reconstructed image.

10. A dose indicator for use in a system for performing radiological procedures using ionizing radiation, comprising:
    a display that displays a graphical representation of an array of individually selectable zones representing areas of skin of a subject exposed during a radiological procedure, wherein each zone is indicative of a different predetermined physical orientation of the subject for the radiological procedure, the display alternatively displays a value of dose associated with only one of the zones when the one of the zones is selected, and the displayed value represents the dose received in an area of skin corresponding to the selected zone exposed during the procedure.

11. The dose indicator as claimed in claim 10 wherein the zones are depicted as the commonly sized areas of skin on the subject exposed during the radiological procedure by use of the commonly used rotation and angulation applied within the system for the procedure.

12. The dose indicator as claimed in claim 10 wherein the values of dose are displayed graphically with the zones.

13. The dose indicator as claimed in claim 10 wherein the values of dose are displayed in units of Air Kerma.

14. The dose indicator as claimed in claim 10, wherein the zones represent an area of skin which is at least 10 cm$^2$.

15. The dose indicator as claimed in claim 10 wherein the zones represent an area of skin which is at least 10 cm by 15 cm.

16. The dose indicator as claimed in claim 10 wherein a graphical form of the display changes when the values of the dose pass a predefined threshold.

17. A user interface for a system for performing radiological procedures comprising a dose indicator according to claim 10.

18. A workstation for a system for performing radiological procedures comprising a dose indicator according to claim 10.

19. The dose indicator as claimed in claim 10, wherein the graphical representation is not a reconstructed image.

* * * * *